(12) United States Patent
Petereit et al.

(10) Patent No.: US 7,498,044 B2
(45) Date of Patent: Mar. 3, 2009

(54) DOSAGE FORM AND METHOD FOR PRODUCING THE SAME

(75) Inventors: Hans-Ulrich Petereit, Darmstadt (DE); Christian Meier, Darmstadt (DE); Klaus Schultes, Wiesbaden (DE)

(73) Assignee: Roehm GmbH & Co. KG, Darmstadt (DE)

( * ) Notice: Subject to any disclaimer, the term of this patent is extended or adjusted under 35 U.S.C. 154(b) by 850 days.

(21) Appl. No.: 10/512,860

(22) PCT Filed: Mar. 2, 2004

(86) PCT No.: PCT/EP2004/002061

§ 371 (c)(1), (2), (4) Date: Nov. 15, 2004

(87) PCT Pub. No.: WO2004/096185

PCT Pub. Date: Nov. 11, 2004

(65) Prior Publication Data

US 2005/0152977 A1    Jul. 14, 2005

(30) Foreign Application Priority Data

Apr. 29, 2003    (DE) ................. 103 19 458

(51) Int. Cl.
*A61K 9/14*    (2006.01)
*A61K 9/16*    (2006.01)
*A61K 9/20*    (2006.01)
*A61K 9/48*    (2006.01)

(52) U.S. Cl. ............ 424/489; 424/451; 424/464; 424/484; 424/490

(58) Field of Classification Search ............ None
See application file for complete search history.

(56) References Cited

U.S. PATENT DOCUMENTS

| | | | |
|---|---|---|---|
| 5,292,522 A * | 3/1994 | Petereit et al. ............ 424/490 |
| 5,548,033 A | 8/1996 | Vetter et al. | |
| 5,644,011 A | 7/1997 | Lehmann et al. | |
| 5,705,189 A | 1/1998 | Lehmann et al. | |
| 5,837,780 A | 11/1998 | Albrecht et al. | |
| 5,993,849 A * | 11/1999 | Assmus et al. ............ 424/449 |
| 6,040,387 A | 3/2000 | Albrecht et al. | |
| 6,063,399 A | 5/2000 | Assmus et al. | |
| 6,287,470 B1 | 9/2001 | Vetter et al. | |
| 6,555,195 B1 | 4/2003 | Zietek et al. | |
| 6,576,255 B1 | 6/2003 | Petereit et al. | |
| 6,632,454 B2 | 10/2003 | Beckert et al. | |
| 6,803,416 B2 | 10/2004 | Schultes et al. | |
| 6,878,387 B1 | 4/2005 | Petereit et al. | |
| 2002/0160042 A1 | 10/2002 | Petereit et al. | |
| 2003/0060381 A1 | 3/2003 | Meier et al. | |
| 2003/0152627 A1 | 8/2003 | Beckert et al. | |
| 2004/0104501 A1 | 6/2004 | Petereit et al. | |
| 2005/0019381 A1 | 1/2005 | Petereit et al. | |
| 2005/0089571 A1 | 4/2005 | Beckert et al. | |
| 2005/0152977 A1 | 7/2005 | Petereit et al. | |
| 2005/0154165 A1 | 7/2005 | Petereit et al. | |

FOREIGN PATENT DOCUMENTS

| | | |
|---|---|---|
| DE | 100 13 030 | 9/2001 |
| DE | 10208335 A1 * | 9/2003 |
| EP | 0 704 207 | 4/1996 |
| WO | 03/032958 | 4/2003 |
| WO | 03/072087 | 9/2003 |

OTHER PUBLICATIONS

U.S. Appl. No. 09/515,098, filed Feb. 29, 2000, Assmus et al.
U.S. Appl. No. 09/868,644, filed Jun. 28, 2001, Hoess et al.
U.S. Appl. No. 10/512,860, filed Nov. 15, 2004, Petereit et al.
U.S. Appl. No. 10/532,831, filed Apr. 26, 2005, Petereit et al.

* cited by examiner

*Primary Examiner*—S. Tran
(74) *Attorney, Agent, or Firm*—Oblon, Spivak, McClelland, Maier & Neustadt, P.C.

(57) ABSTRACT

The invention relates to a process for producing a coated drug form or a drug form in the form of an active ingredient matrix, by processing a copolymer, an active pharmaceutical ingredient, a core if present and/or pharmaceutically customary excipients in a conventional manner by melting, injection molding, extrusion, wet granulation, casting, dipping, spreading, spraying or compression to form a coated drug form and/or to form an active ingredient matrix, characterized in that a copolymer is used which is composed of 20 to 33% by weight methacrylic acid, 5 to 30% by weight methyl acrylate, 20 to 40% by weight ethyl acrylate and more than 10 to 30% by weight butyl methacrylate and, if desired, 0 to 10% by weight further vinylically copolymerizable monomers, with the proviso that the glass transition temperature of the copolymer in accordance with ISO 11357-2, section 3.3.3, is 55 to 70° C. The invention further relates to the drug form produced in accordance with the invention, to the copolymer, and to the use thereof.

18 Claims, No Drawings

DOSAGE FORM AND METHOD FOR PRODUCING THE SAME

This application is a national stage application of International Patent Application No. PCT/EP04/02061 filed on Mar. 2, 2004, and claims priority to German Patent Application No. 103 19 458.4, filed on Mar. 29, 2003, both of which are incorporated herein by reference in their entireties.

The invention relates to a process for producing drug forms, to the drug forms themselves, to the copolymer present therein, and to its use for producing the drug form.

PRIOR ART

EP 0 704 208 A2 describes coating agents and binders for drug coverings soluble in intestinal juice. These comprise copolymers of 10 to 25% by weight methacrylic acid, 40 to 70% by weight methyl acrylate and 20 to 40% by weight methyl methacrylate. As well as monolayer coatings, the description mentions multilayer coating systems. These may be composed of a core, comprising for example a basic or a water-sensitive active ingredient, may have an insulating layer of another coating material, such as cellulose ethers, cellulose esters or a cationic polymethacrylate of the EUDRAGIT® type, for example, including EUDRAGIT® RS and RL, and are then additionally provided with the abovementioned covering soluble in intestinal juice.

EP 0 704 207 A2 describes thermoplastic materials for drug coverings soluble in intestinal juice. These comprise copolymers of 16 to 40% by weight acrylic or methacrylic acid, 30 to 80% by weight methyl acrylate and 0 to 40% by weight other alkyl esters of acrylic acid and/or methacrylic acid. The minimum film-forming temperature (MFT according to DIN 53 778) is in the range between 0 and 25° C., so that processing is possible at room temperature without adding plasticizer. The breaking elongation of the films, measured in accordance with DIN 53 455, is generally 50% or more at a maximum triethyl citrate content of 10% by weight.

PROBLEM AND SOLUTION

EP 0 704 207 A2 and EP 0 704 208 A2 describe copolymers for producing drug forms based on (meth)acrylate monomers, which form comparatively flexible films and have release profiles that are suitable for many drugs in the range of high pH values above about 6.0.

The permanently ongoing development of drug forms is increasingly demanding better and better coating agents and binders. Coating agents and binders are being developed which, sometimes in conjunction with further additives, are allowing increasingly more specific release characteristics, tailored to the respective active ingredient.

Another trend in development, however, is generally to minimize the fraction of additives as compared with the active ingredient itself. In the case of drug forms with a functional coating, therefore, the aim is to reduce the thickness of the coating. This has its limits, firstly in the target release characteristics for the drug itself and secondly in the mechanical stability of the coatings. With very thin coatings there is always a risk of mechanical damage in the course of production or storage.

Furthermore, even today many active ingredients are provided in the form of multiparticulate drug forms. As a result of the amount of particles present in a drug form, success is being achieved in limiting fluctuations in dosage caused by fluctuating thicknesses of the functional coatings. Since the production of multiparticulate drug forms is carried out by compressing coated pellets containing active substance together with auxiliaries under pressures which are in some cases high, many otherwise very suitable polymeric coating agents are not appropriate for this drug form, since they do not withstand the mechanical loads with sufficient reliability or withstand them only when the coatings are applied with a disproportionate thickness.

EP 0 704 207 A2 and EP 0 704 208 A2 describe copolymers for producing drug forms based on (meth)acrylate monomers, which form comparatively flexible films and have release profiles that are suitable for many drugs in the range of high pH values above about 6.0. As has been found, the copolymers described specifically by EP 0 704 207 A2 have poor resistance, at least to relatively high mechanical loads. The polymers described in EP 0 704 208 A2, however, dissolve only above a pH of 6.5, and hence in relatively low sections of the intestine. They are therefore unsuitable for active ingredients whose absorption takes place preferably in the upper regions of the intestine.

The problem was seen as being to provide drug forms soluble in intestinal juice which do not release the active ingredient until a pH of about 5.8 to about 6.0 and which at the same time form mechanically stable, nontacky films without disproportionate addition of plasticizer. In particular the intention was to provide formulations which satisfy the stringent mechanical requirements associated with the production of multi-particulate drug forms.

The problem is solved by a process for producing a coated drug form or a drug form in the form of an active ingredient matrix, by processing a copolymer, an active pharmaceutical ingredient, a core if present and/or pharmaceutically customary excipients in conventional manner by melting, injection molding, extrusion, wet granulation, casting, dipping, spreading, spraying or compression to form a coated drug form and/or to form an active ingredient matrix, characterized in that a copolymer is used which is composed of 20 to 33% by weight methacrylic acid and/or acrylic acid, 5 to 30% by weight methyl acrylate and 20 to 40% by weight ethyl acrylate and more than 10 to 30% by weight butyl methacrylate and, if desired, 0 to 10% by weight further vinylically copolymerizable monomers, the proportions adding up to 100% by weight, with the proviso that the glass transition temperature of the copolymer in accordance with ISO 11357-2, section 3.3.3, is 55 to 70° C.

The invention further provides the drug form itself and also the copolymer and its use for producing the drug form.

IMPLEMENTATION OF THE INVENTION

The invention relates to a process for producing a drug form in the form of a tablet, drug form comprising pellets and/or active ingredient matrix, the tablets, pellets and/or active ingredient matrix comprising an active pharmaceutical substance and a copolymer as coating agent and/or binder, and, if desired, a core and pharmaceutically customary excipients, by processing the copolymer, the active pharmaceutical ingredient, the core if present and/or the pharmaceutically customary excipients in conventional manner, by melting, injection molding, extrusion, wet granulation, casting, spreading, spraying or compression to form tablets or pellets and/or an active ingredient matrix.

Copolymer

Key to the invention is the use of a copolymer which is composed of 20 to 33% by weight methacrylic acid and/or acrylic acid,
5 to 30% by weight methyl acrylate and
20 to 40% by weight ethyl acrylate and
more than 10 to 30% by weight butyl methacrylate and, if desired,
0 to 10% by weight further vinylically copolymerizable monomers,
the proportions of the monomers adding up to 100% by weight, with the proviso that the glass transition temperature of the copolymer in accordance with ISO 11357-2, point 3.3.3 (midpoint temperature $T_{mg}$), is 55 to 70° C.

The copolymer is composed in particular of free-radically polymerized units of 20 to 33%, preferably 25 to 32%, more preferably 28 to 31% by weight methacrylic acid or acrylic acid; methacrylic acid is preferred;
5 to 30%, preferably 10 to 28%, more preferably 15 to 55% by weight methyl acrylate,
20 to 40%, preferably 25 to 35%, more preferably 18 to 22% by weight ethyl acrylate, and
more than 10 to 30%, preferably 15 to 25%, more preferably 18 to 22% by weight butyl methacrylate, the monomer composition being chosen such that the glass transition temperature of the copolymer is 55 to 70° C., preferably 59 to 66° C., more preferably 60 to 65° C.

By glass transition temperature is meant here in particular the midpoint temperature $T_{mg}$ in accordance with ISO 11357-2, section 3.3.3. The measurement is made without addition of plasticizer, at residual monomer contents (REMO) of less than 100 ppm, at a heating rate of 10° C./min and under a nitrogen atmosphere.

The copolymer is preferably composed essentially to exclusively, to an extent of 90%, 95% or 99% to 100% by weight, of the monomers methacrylic acid, methyl acrylate, ethyl acrylate and butyl methacrylate in the quantity ranges indicated above.

Additionally, however, it is possible, without this necessarily leading to any deterioration in the essential properties, for small amounts, in the range from 0 to 10%, e.g., from 1 to 5% by weight, of further vinylically copolymerizable monomers to be present, such as methyl methacrylate, butyl acrylate, hydroxyethyl methacrylate, vinylpyrrolidone, vinyl-malonic acid, styrene, vinyl alcohol, vinyl acetate and/or derivatives thereof, for example.

Preparation of the Copolymer

The copolymer can be prepared in conventional manner by free-radical addition polymerization of the monomers (see, e.g., EP 0 704 207 A2 and EP 0 704 208 A2). The copolymer of the invention is preparable in a conventional manner by free-radical emulsion polymerization in aqueous phase in the presence of preferably anionic emulsifiers, by the process described in DE-C 2 135 073, for example.

The copolymer can be prepared by customary methods of free-radical polymerization continuously or batchwise in the presence of free-radical initiators and, if desired, regulators for adjusting the molecular weight, in bulk, in solution, by bead polymerization or in emulsion. The average molecular weight Mw (weight average, determined for example by measuring the solution viscosity) can be, for example, in the range from 80 000 to 1 000 000 (g/mol). Preference is given to emulsion polymerization in aqueous phase in the presence of water-soluble initiators and (preferably anionic) emulsifiers.

In the case of bulk polymerization the copolymer can be obtained in solid form by crushing, extrusion, granulation or hot chopping.

Organic Solution

The copolymer can be provided in the form of an organic solution, in a concentration of from 10 to 30% by weight, for example. Solvents which can be used include, for example, acetone, isopropanol or ethanol or mixtures thereof, which may where appropriate include water fractions of up to about 10% by weight. Preference is given, however, to aqueous dispersions.

Dispersions

The emulsion polymer is preferably produced and employed in the form of an aqueous dispersion with a concentration of from 10 to 50 percent by weight, in particular from 20 to 40 percent by weight. A preferred commercial form is a solids content of 30% by weight. For processing, partial neutralization of the meth-acrylic acid units is not vital; it is possible, however, in an extent of up to 5 or 10 mol %, for example, if stabilization or thickening of the coating agent dispersion should be desired. The weight average value of the latex particle size (radius) is generally from 40 to 100 nm, preferably from 50 to 70 nm, which ensures a favorable processing viscosity of less than 1000 mPa·s. The particle size can be determined by laser diffraction, using for example a Mastersizer 2000 (Malvern).

At a relatively high degree of neutralization of from 10 to 50 mol %, for example, or in the case of full neutralization it is possible to convert the copolymer into a dissolved state.

In order to prepare a solution of the anionic copolymer it is generally necessary for the acid groups to be partly or fully neutralized. The anionic copolymer can be stirred into water, for example, gradually in a final concentration of from 1 to 40% by weight, in the course of which it can be partly or fully neutralized by addition of a basic substance such as NaOH, KOH or ammonium hydroxide, for example, or organic bases such as triethanolamine, for example. It is also possible to use a powder of the copolymer to which a base—NaOH, for example—has already been added in the course of its preparation for the purpose of (partial) neutralization, so that the powder is an already (partially) neutralized polymer. The pH of the solution is generally above 4, in the range from 4 to about 7 for example. It is also possible in this context to make, for example, mixtures of batches of fully or partly neutralized dispersions with unneutralized dispersions and to process such mixtures further in the manner described, in other words to use the mixture for coatings or first to freeze- or spray-dry it to a powder.

The dispersion can, for example, also be spray-dried or freeze-dried in conventional manner and provided in the form of a redispersible powder (see e.g. EP-A 0 262 326). Alternative methods are those of freeze drying or coagulation and removal of the water by squeezing in an extruder with subsequent granulation (see e.g. EP-A 0 683 028).

Surprisingly it has been found that copolymer dispersions formed from spray-dried or freeze-dried and redispersed powders exhibit an increased shear stability. This is an advantage particularly in the context of spray application. This advantage is manifested to a particularly high extent when the copolymer present in the dispersion is from 2 to 10 mol %, preferably 5 to 7 mol %, in partially neutralized form (based on the acid groups present in the copolymer). Preference is given for this purpose to partial neutralization by adding NaOH. There is preferably an anionic emulsifier present in an amount of from 0.1 to 2% by weight. Particular preference is given to sodium lauryl sulfate as emulsifier.

Ready to Use

The copolymer can be present in powder form in a mixture with customary pharmaceutical excipients in a readily redispersible form. If the starting product is a copolymer powder, an already partially neutralized powder, for example, then this powder can be ground and/or mixed and/or formulated dry with customary pharmaceutical excipients, such as talc, soluble dyes, dye pigments or stabilizers, for example. The formulation is referred to as a ready to use formulation, which following addition of water and a comparatively short redispersing time can be used directly as a ready-made or at least substantially complete coating agent or binder.

Mechanical Properties

In the area of the copolymer composition selected in accordance with the invention a sudden increase in mechanical stability, that is to say the shear strength in particular, is found. The mechanical stability of the copolymer, even without plasticizer, is distinctly improved as compared with noninventive copolymers of similar composition but with a higher glass transition temperature. Noninventive copolymers of similar composition and with glass transition temperatures of 55-70° C., moreover, no longer have the desired release profile.

The differences are manifested to a particular extent when plasticizer is added. From a level of 1% by weight of plasticizer upward, differences in the breaking elongation behavior (in accordance with DIN 53 455) are already measurable. The copolymer can contain 0 to 40% by weight plasticizer. Generally 6 to 30%, preferably 15 to 25% by weight plasticizer is favorable. The plasticizer-containing copolymer can have breaking elongation values [%] of at least 250, at least 300, at least 400, 250 to 500 or 300 to 450.

Polymer Mixtures

In order to control the release of active ingredient it may in certain cases be advantageous to mix other polymers into the copolymer. The fraction of other polymers in the mixture can vary within wide ranges and lies between 5 and 95%, preferably 10 and 90% by weight, more preferably between 25 and 85% by weight.

Examples of such other polymers are: polyvinyl-pyrrolidones, polyvinyl alcohols,. anionic(meth)acrylate copolymers of methyl methacrylate and/or ethyl acrylate and methacrylic acid (EUDRAGIT® L 100, EUDRAGIT® S 100, EUDRAGIT® L 100-55). Anionic (meth)acrylate copolymers of methyl methacrylate, methyl acrylate and methacrylic acid of the prior art (see, for example, EP-A-0 704 207 or EP-A-0 704 208), carboxymethylcellulose salts, hydroxypropylcellulose (HPMC), neutral (meth)acrylate copolymers of methyl methacrylate and ethyl acrylate (dry substance from EUDRAGIT® NE 30 D), copolymers of methyl methacrylate and butyl methacrylate (PLASTOID® B) or (meth)acrylate copolymers containing quaternary ammonium groups (EUDRAGIT® RL or EUDRAGIT® RS).

Multilayer Drug Forms

In order to control the release of active ingredient it may be advantageous in certain cases to provide the drug form with further polymer or copolymer layers which may be arranged within or outside a layer containing the copolymer of the invention. It is possible, for example, to add an outer release delay layer or a further outer enteric and/or taste-insulating layer. A further example of this would be the application of an outer colored polymer layer, composed for example of hydroxypropylmethylcellulose (HPMC) and dyes.

Examples of such further polymers are: polyvinyl-pyrrolidones, polyvinyl alcohols, anionic (meth)acrylate copolymers of methyl methacrylate and/or ethyl acrylate and methacrylic acid (EUDRAGIT® L 100, EUDRAGIT® S 100, EUDRAGIT® L 100-55). Anionic (meth)acrylate copolymers of methyl methacrylate, methyl acrylate and methacrylic acid of the prior art (see, for example, EP-A-0 704 207 or EP-A-0 704 208), carboxymethylcellulose salts, hydroxypropylmethyl-cellulose (HPMC), neutral (meth)acrylate copolymers of methyl methacrylate and ethyl acrylate (dry substance from EUDRAGIT® NE 30 D), copolymers of methyl methacrylate and butyl methacrylate (PLASTOID® B) or (meth)acrylate copolymers containing quaternary ammonium groups (EUDRAGIT® RL or EUDRAGIT® RS).

Drug Form

The drug form of the invention is in the form of a tablet, drug form comprising pellets and/or in the form of an active ingredient matrix, the tablets, pellets and/or active ingredient matrix comprising an active pharmaceutical substance and a copolymer as coating agent and/or binder, and, if desired, a core and pharmaceutically customary excipients. (Film-coated) tablets normally comprise active ingredient cores coated with a copolymer; pellets are generally composed of coated cores or else of coated crystals of active ingredient. In an active ingredient matrix the copolymer acts as a binder for the active ingredient.

The term "drug form in the form of a tablet, drug form comprising pellets and/or in the form of an active ingredient matrix" is intended to comprehend all common types of drug forms of which the skilled worker is aware. The forms in question include, in particular, tablets, including tablets with retarded or accelerated disintegration, minitablets, pellets, to be understood to include granules, microparticles or microtablets, tablets compressed to form pellets (multiparticulate drug form), pellets as a filling in capsules, minitablets and granules. Transdermal therapy systems in the form, for example, of a patch or a coating are examples of active ingredient matrices. The forms may also be capsules, parts of capsules or other drug forms, sachets, dry juices, suppositories, pessaries or implants.

In accordance with the process of the invention the copolymer, in combination if desired with pharmaceutically customary adjuvants, e.g., plasticizers, mold release agents and/or dyes, can also first be processed to form shaped bodies and then an active pharmaceutical ingredient, with or without a core, can be enclosed therein. This processing may take place preferably by dipping, injection molding or extrusion. The shaped body may be a capsule, the part of a capsule or a weldable film.

Production of the Drug Form

The drug form is prepared by processing the copolymer, the active pharmaceutical ingredient, the core if present and/or the pharmaceutically customary excipients in conventional manner, with or without the addition of water, by melting, injection molding, extrusion, wet granulation, casting, spreading, spraying or compression to form tablets or drug forms comprising pellets and/or to form an active ingredient matrix.

Further Uses

As well as being used for drug forms, the copolymer of the invention can also be used as a constituent or ingredient of cosmetics or nutritional supplements. Within the field of cosmetics the copolymer can be incorporated preferably in dissolved form into ointments and creams, for example, or as a constituent of cosmetic patches. In the case of the nutritional supplements the copolymer can be used, for example, for taste insulation, as a covering for protecting vitamins or minerals, and for insulating incompatible constituents.

Active Ingredients

The active ingredients used for the purposes of the invention are intended to be used on or in the human or animal body in order
1. to heal, alleviate, prevent or diagnose diseases, ailments, physical damage or pathological symptoms.
2. to allow the state, condition or functions of the body, or mental states, to be identified.
3. to replace active substances or body fluids produced by the human or animal body.
4. to defend against, eliminate or render innocuous pathogens, parasites or exogenous substances, or
5. to influence the state, condition or functions of the body, or mental states.

Drugs in common use can be found in reference works, such as the Rote Liste or the Merck Index, for example. In accordance with the invention it is possible to use any active ingredients which fulfill the desired therapeutic activity in the sense of the above definition and which possess a sufficient thermal stability.

The formulation of the invention is suitable for administering in principle any active pharmaceutical ingredients which are to be released preferentially in the intestine and/or colon, and particularly those which may be administered advantageously in delayed-release form.

Particular mention should be made of active ingredient from the following class of active ingredients: laxatives, analgesics, antibiotics, antirheumatics, antiallergics, antiarrhythmics, antibiotics, antiepileptics, beta-receptor blockers, calcium channel blockers, chemotherapeutics, enzymes, extracts, inhibitors of the rennin-angiotensin system, broncholytics/antasthmatics cholinergics, diuretics, circulation promoters, gout agents influenza agents, coronary agents, osteoporosis agents (biphosphonates), lipid reducers, gastrointestinal agents, peptides, proteins, proton pump blockers, psychopharmaceuticals, platelet aggregation inhibitors urological agents venous therapeutic agents, vitamins and minerals.

The drug form of the invention may comprise, for example, the following active ingredients: characterized in that as active ingredient paroxetine, reboxetine morphine and its derivatives, tramadol, bisacodyl, sodium fluoride acamprosate Ca, digitoxin, dimethicone, coli bacteria, liponic acid, methenamine, budenoside, acetylsalicylic acid, diclofenac, flurbiprophen, indometacin, lonazolac, hydrocortisone, ibuprofen, ketoprofen, prednisolone, propyphenazone, naproxen, paracetamol, flurbiprofen, dimetindene, quinidine, metoprolol, propranolol, oxprenolol, pindolol, atenolol, metoprolol, disopyramide, verapamil, diltiazem, gallopamil, nifedipine, nicardipine, nisoldipine, nimodipine, amlodipine, theophylline, salbutamol, terbutaline, ambroxol, aminophylline, carbamazepine, alendronate, etidronate, clodronate, pamidronate, ibandronate choline theophyllinate, pyridostigmine, piretanide, furosemide, pentoxyifylline, naftidrofuryl, buflomedil, xantinol nicotinate, bencyclane, allopurinol, norephedrine, clorphenamine isosorbide mononitrate, isosorbide dinitrate, glycerol trinitrate, molsidomine, bezafibrate, fenofibrate, gemfibrozil, cerivastatin, pravastatin, fluvastatin, lovastatin, atorvastatin, simvastatin, 5-aminosalicylic acid, sulfasalazine, budenoside, natamycin, preglumetacin sulfasalacine, nitrofurantion xantinol, metoclopramid, amitriptyline, dibenzepine, venlafaxin, thioridazine, oxazepam, omeprazole, lanzoprazole, pantoprazole, rabeprazole, perprazole, esomprazole, nitrofurantoin, rutoside, garlic, aescin, bromelaine, pancreatin or trypsin, an insulin, a human growth hormone (hGH), corbaplatin, intron A, calcitonin, cromalyn, an interferon, a calcitonin, granulocyte colony stimulating factor (G-CSF), an interleukin, a kinine, parathyroid hormones, glucagon, pindolol, prosomatostatin, a somatostatin, detirelix, cetrorelix, vasopressin, 1-deaminocysteine-8-D-arginine vasopressin, leuprolide acetate or an antigen obtained from grasses or other plants, such as rye, wheat, barley, oats, Bermuda grass, horsetail, maple, elm, oak, plane, poplar, cedar, horsetail, thistles, IgG, specific vaccines or monoclonal antibodies, dry plant extract, ascorbic acid, aspartamic acid, valproic acid zinc, and potassium, sodium, lithium and their salts used pharmaceutically.

The active ingredients can if desired also be used in the form of their pharmaceutically acceptable salts or derivatives, and in the case of chiral active ingredients not only optically active isomers but also racemates or diastereoisomer mixtures can be used. If desired the compositions of the invention may also comprise two or more active pharmaceutical ingredients.

Pharmaceutically Customary Excipients a) Plasticizers
Substances suitable as plasticizers generally have a molecular weight of between 100 and 20 000 and contain one or more hydrophilic groups in their molecule, e.g., hydroxyl, ester or amino groups. Suitability is possessed by citrates, phthalates, sebacates and castor oil. Examples of suitable plasticizers are alkyl citrates, glycerol esters, alkyl phthalates, alkyl sebacates, sucrose esters, sorbitan esters and polyethylene glycols 4000 to 20 000. Preferred plasticizers are tributyl citrate, triethyl citrate, acetyl triethyl citrate, dibutyl sebacate and diethyl sebacate. It is preferred to add up to 30%, in particular 5 to 25% by weight of a plasticizer to the copolymer, based on the dry weight of the copolymer.

b) Further Pharmaceutically Customary Excipients
Mention may be made here of, for example, stabilizers, dyes, antioxidants, wetting agents, pigments, gloss agents, etc. They serve primarily as processing assistants and are intended to ensure the possibility of a reliable and reproducible production process and good long-term storage stability. Pharmaceutically customary excipients can be present in amounts from 0.001% by weight to 300% by weight, preferably 0.1 to 100% by weight, based on the copolymer.

Examples of dry standardizers are: alumina, magnesium oxide, kaolin, talc, silica (Aerosils), barium sulfate, carbon black and cellulose.

Unlike dry standardizers, mold release agents have the property of reducing the force of adhesion between the moldings and the surface of the device in which the drug form is produced. This makes it possible to produce moldings which are not crushed and have not undergone geometrical deformation. Mold release agents are generally partly compatible or incompatible with the polymers in which they are particularly effective. As a result of the partial compatibility or incompatibility, the injection of the melt into the mold cavity is accompanied by migration into the interface of the transition between mold wall and molding. In order that mold release agents can migrate with particular advantage, the melting point of the mold release agent must be 20° C. to 100° C. below the processing temperature of the polymer.

Examples of (mold) release agents are: esters of fatty acids or fatty acid amides, aliphatic long-chain carboxylic acids, fatty alcohols and their esters, montan waxes or paraffin waxes and metal soaps, of which mention may be made in particular of glycerol monostearate, stearyl alcohol, glycerol behenates, cetyl alcohol, palmitic acid, carnauba wax, beeswax, etc.

Production of Multiparticulate Drug Forms

The invention is particularly suitable for producing multiparticulate drug forms, since the copolymer of the invention withstands the high pressures accompanying the compression of the pellets with the filler.

The production of multiparticulate drug forms by compression of a pharmaceutically customary binder with active ingredient particles is described in detail in, for example, Beckert et al. (1996), "Compression of enteric-coated pellets to disintegrating tablets", *International Journal of Pharmaceutics* 143, pp. 13-23, and in WO 96/01624.

Active ingredient pellets can be produced by applying an active ingredient by means of a layering operation. For that purpose active ingredient is homogenized together with further excipients (release agents, plasticizers if appropriate) and dissolved or suspended in a binder. The liquid can be applied to placebo pellets or other suitable carrier materials by means of a fluid-bed process, the solvent or suspension medium being evaporated (reference: *International Journal of Pharmaceutics* 143, pp. 13-23). The production process may be followed by a drying step. The active ingredient can be applied in a number of layers.

Some active ingredients, acetylsalicylic acid being one example, are commercially customary in the form of active ingredient crystals and can be used in that form instead of active ingredient pellets.

Film coatings on active ingredient pellets are normally applied in fluid-bed devices. Formula examples are mentioned in this specification. Film formers are normally mixed with plasticizers and release agents by a suitable method. The film formers may be present in this context as a solution or suspension. The film-forming auxiliaries may likewise be in solution or suspension. Organic or aqueous solvents or dispersion media may be used. In order to stabilize the dispersion it is possible additionally to use stabilizers (example: Tween 80 or other suitable emulsifiers and/or stabilizers).

Examples of release agents are glycerol monostearate or other suitable fatty acid derivatives, silica derivatives or talc. Examples of plasticizers are propylene glycol, phthalates, polyethylene glycols, sebacates or citrates, and other substances mentioned in the literature.

Applied between the active ingredient layer and gut-soluble copolymer layer there may be a separating layer which serves to separate active ingredient and coating material for the purpose of preventing interactions. This layer may be composed of inert film formers (e.g., HPMC, HPC or (meth)acrylic acid copolymers) or, for example, talc or other suitable pharmaceutical substances. It is also possible to use combinations of film formers and talc or similar substances.

It is also possible to apply a separating layer composed of partly or fully neutralized copolymer dispersions.

Mixtures for producing tablets from coated particles are prepared by mixing the pellets with suitable binders for tableting, if necessary adding disintegration promoters, and if necessary adding lubricants. Mixing can take place in suitable machines. Unsuitable mixers are those which lead to damage to the coated particles, plowshare mixers being an example. In order to obtain suitable short disintegration times a specific sequence may be necessary in the addition of the auxiliaries to the coated particles. By premixing magnesium stearate as lubricant or mold release agent with the coated particle it is possible to hydrophobicize the surface of said particle and so to prevent sticking.

Mixtures suitable for tableting normally contain 3 to 15% by weight of a disintegration assistant, e.g., Kollidon CL and, for example, 0.1 to 1% by weight of a lubricant and mold release agent such as magnesium stearate. The binder fraction is determined in accordance with the required fraction of coated particles.

Examples of typical binders include Cellactose®, microcrystalline cellulose, calcium phosphates, Ludipress®, lactose or other suitable sugars, calcium sulfates or starch derivatives. Preference is given to substances having a low bulk density.

Typical disintegration assistants (disintegrants) are crosslinked starch derivatives or cellulose derivatives, and also crosslinked polyvinylpyrrolidone.

Cellulose derivatives are also suitable. Through the selection of an appropriate binder it may be possible to do without the use of disintegration assistants.

Typical lubricants and mold release agents are magnesium stearates or other suitable salts of fatty acids or substances listed in the literature for this purpose (e.g., lauric acid, calcium stearate, talc, etc). Where suitable machines (e.g., tableting press with external lubrication) or suitable formulations are used it may be unnecessary to use a lubricant and mold release agent in the mixture.

An auxiliary to improve flow may be added to the mixture if desired (e.g., highly disperse silica derivatives, talc, etc).

Tableting can take place on customary tableting presses, eccentric or rotational tableting presses, under compression forces in the range from 5 to 40 kN, preferably 10-20 kN. The tableting presses may be equipped with systems for external lubrication. Where appropriate, special systems are employed for die charging which avoid die charging by means of stirring paddles.

Further Production Processes for the Drug Form of the Invention

Application process takes place by means of spray application from organic solution, or preferably aqueous dispersions by melting or by direct powder application. The critical factor for the version is that uniform, pore-free coatings are formed.

Application processes in accordance with the state of the art see for example Bauer, Lehmann, Osterwald, Rothgang, "Überzogene Arzneiformen" Wissenschaftliche Verlagsgesellschaft mbH Stuttgart, chap. 7, pp. 165-196.

For the application, relevant properties, required tests and specifications are listed in pharmacopeias.

Details can be found in common textbooks, e.g.:

Voigt, R. (1984): Lehrbuch der pharmazeutischen Technologie; Verlag Chemie Weinheim—Beerfield Beach/Fla.—Basel.

Sucker, H., Fuchs, P., Speiser, P.: Pharmazeutische Technologie, Georg Thieme Verlag Stuttgart (1991), especially chapters 15 and 16, pp. 626-642.

Gennaro, A. R., (Editor), Remington's Pharmaceutical Sciences, Mack Publishing Co., Easton Pa. (1985), chapter 88, pp. 1567-1573.

List, P. H. (1982): Arzneiformeniehre, Wissenschaftliche Verlagsgesellschaft mbH, Stuttgart.

ADVANTAGEOUS EFFECTS OF THE INVENTION

A rapid release of active ingredient with simultaneous insulation of the active ingredient, taste protection and/or odor protection can be achieved, for example, in thinly covered drug forms or cosmetics or nutritional supplements. In this case the coat thicknesses are, for example, in the range from 1 to 15 μm.

A slightly delayed release of active substance in stomach and intestine can be achieved, for example, in covered drug forms or cosmetics or nutritional supplements. In this case the coat thicknesses are, for example, in the range from 15 to 40 μm. The copolymer film or copolymer matrix is advantageously dissolved at a pH below 6.0.

Gastric juice resistance and, where appropriate, an increase in bioavailability can be achieved, for example, in covered drug forms or cosmetics or nutritional supplements. In this case the coat thicknesses are, for example, in the range from 40 to 60 μm.

Active ingredient release in deeper sections of the intestine and, where appropriate, an increase in bioavailability can be achieved, for example, in covered drug forms or cosmetics or nutritional supplements. In this case the coat thicknesses are, for example, in the range from 70 to 100 μm.

Accelerated release in conjunction with an increase in bioavailability can be achieved from matrix systems in which the copolymer fraction in % by weight is greater than the active ingredient fraction.

Copolymer films have a high breaking elongation and are therefore sufficiently elastic without added plasticizer or even with a low level of plasticizer addition. Copolymer dispersions can be prepared which have very little propensity, if any, to form coagula. The dispersions are therefore very reliable in processing and stable on storage.

EXAMPLES

Example 1

Comparison of Properties of Inventive and Noninventive Copolymers

3=severe formation of coagulum in the sieve and on the magnetic stirrer (unacceptable)

Copolymers A to C are inventive copolymers.

Copolymers A to C are distinguished by good (A and B) to still just acceptable (C) breaking elongation values. The effect of the glass transition temperature in the range from 55 to 70° C. is that the polymers have good mechanical stability.

Copolymer V1 to V6 are noninventive copolymers.

In the case of copolymer V1 the monomer composition is indeed within the proportions according to the invention, but the proportions have been chosen so that the as-claimed proviso of the upper glass transition temperature limit of 70° C. is exceeded. Consequently the copolymer is too hard and the breaking elongation is unsatisfactory.

In the case of copolymer V2 the butyl methacrylate monomer is absent. The absence of this monomer implies a propensity on the part of resulting dispersions toward coagulation.

In the case of copolymer V3 the proportion required for methacrylic acid as per the claims is exceeded. The consequence is a marked drop in breaking elongation.

In the case of copolymer V4 the proportion of butyl methacrylate is just outside the required limit. A slight propensity toward formation of coagulum is present, and as a result the desired processing reliability is no longer regarded as being given.

Copolymer V5 (EUDRAGIT® L30D-55) contains no methyl methacrylate and also no butyl methacrylate and has a very low breaking elongation in conjunction with a very high glass transition temperature. Copolymer V5 therefore needs

| Copolymer | A | B | C | V1 | V2 | V3 | V4 | V5 (L30D-55) | V6 (FS30D) |
|---|---|---|---|---|---|---|---|---|---|
| Methacrylic acid | 30 | 30 | 30 | 30 | 30 | 35 | 30 | 50 | 10 |
| Methyl acrylate | 25 | 20 | 15 | 10 | 40 | 18 | 30 | — | 65 |
| Ethyl acrylate | 30 | 30 | 30 | 30 | 30 | 29 | 30 | 50 | — |
| Butyl methacrylate | 15 | 20 | 25 | 30 | — | 18 | 10 | — | — |
| Methyl methacrylate | — | — | — | — | — | — | — | — | 35 |
| Glass transition temperature Tg ° C. [DIN 11357, 3.3.3.] | 56 | 65 | 67 | 73 | 56 | 65 | 61 | 115 | 48 |
| Breaking elongation [%] 20% by weight TEC DIN 53455 | 423 | 296 | 169 | 133 | 320 | 77 | 362 | 10 | 1000 |
| Coagulum formed in the dispersion after | | | | | | | | | |
| 3 h | 0 | 0 | 0 | 0 | 1 | 0 | 1 | 0 | 0 |
| 6 h | 1 | 0 | 0 | 0 | 2 | 0 | 1 | 0 | 0 |
| 24 h | 1 | 0 | 0 | 0 | 3 | 0 | 2 | 0 | 1 |

The breaking elongation [%] was determined in accordance with DIN 53455 with the addition of 20% by weight triethyl citrate (TEC). The formation of coagulum in the dispersion was determined in a stirring test with a magnetic stirrer at room temperature and a stirrer speed of approximately 100 per minute.

The results were evaluated after 3, 6 and 24 h as follows:

0=no coagulum (stipulation for the 3 and 6 h value)

1=slight formation of coagulum in the sieve (not acceptable for the 3 and 6 h value)

2=large quantity of coagulum in the sieve (unacceptable)

high levels of plasticizer addition, well above 20% by weight, in order to achieve acceptable breaking elongation values. In this case, however, there is always a possibility that the properties of the film coating will be influenced undesirably. In certain cases it is possible, for example, for separation phenomena to occur after storage.

Copolymer V6 (EUDRAGIT® FS30D) has a low methacrylic acid content and contains no ethyl acrylate or butyl methacrylate. The glass transition temperature is comparatively low. Copolymer V6 possesses extremely good breaking elongation behavior. This polymer dissolves, however, only at above a pH of 7.0 and therefore possesses an entirely different release profile from the inventive copolymers, which begin to dissolve at a pH of about 6.0.

Example 2

Coating on Quinidine Sulfate Tablets

| | |
|---|---|
| Emulsion polymer copolymer B* | 469.7 g |
| Glycerol monostearate (GMS) | 7.0 g |
| Polysorbat 80 (33% aqueous solution) | 8.5 g |
| Water, purified | 268.7 g |

*(Copolymer B = copolymer of 30% by weight methacrylic acid, 20% by weight methyl acrylate, 30% by weight ethyl acrylate and 20% by weight butyl methacrylate)

are used to prepare a spray suspension, by emulsifying GMS and Polysorbat 80 at 65° C. in the water and cooling the emulsion to room temperature with stirring. The emulsion polymer is incorporated into this emulsion with stirring.

In a 35 cm coating pan (diameter 35 cm) with AR 400 drive (from Erweka, Heusenstamm) and a spray gun (from Schlick, model 970 form 7-1 S 21) a mixture of 2300 g of placebo cores (10 mm diameter, 300 mg weight) and 200 g of quinidine sulfate tablets (5% active substance content, 10 mm diameter, 300 mg weight) are coated under the following conditions:

| | |
|---|---|
| Nozzle diameter | 1.2 mm |
| Pan rotational speed | 40 rpm |
| Feed air temperature | 30-42° C. |
| Product temperature | 28-30° C. |
| Spraying pressure | 0.8 bar |
| Spraying rate | 8-9.5 g/min |
| Afterdrying | 2 h, at 40° C. on racks |

The polymer add-on was 6.0 mg/cm².

The coated quinidine sulfate tablets gave the following results in the dissolution test according to Pharm. Eur.:

| Time [min] | pH | Release [%] |
|---|---|---|
| 10 | 1.2 | <1.0 |
| 60 | 1.2 | <1.0 |
| 120 | 1.2 | <1.0 |
| 140 | 6.8 | 20 |
| 150 | 6.8 | 84 |
| 180 | 6.8 | 100 |

Example 3

Coating on Bisacodyl Pellets

| | |
|---|---|
| Emulsion polymer copolymer B | 53.3 g |
| Glycerol monostearate (GMS) | 1.6 g |
| Polysorbat 80 (33% aqueous solution) | 1.9 g |
| Water, purified | 64.7 g | are used to prepare a spray suspension, by emulsifying GMS and Polysorbat 80 at 65° C. in the water and cooling the emulsion to room temperature with stirring. The emulsion polymer is incorporated into this emulsion with stirring.

In a fluidized-bed apparatus (type: Mini Glatt, from GLATT) 200 g of bisacodyl pellets are coated by means of bottom spraying, under the following conditions:

| | |
|---|---|
| Nozzle diameter | 0.5 mm |
| Feed air temperature | 35° C. |
| Product temperature | 31-32.5° C. |
| Spraying pressure | 0.5 bar |
| Spraying rate | 1.6-1.8 g/min |
| Afterdrying | 2 h, at 40° C. on racks |

The polymer add-on was 8%.

The coated bisacodyl pellets gave the following results in the dissolution test according to Pharm. Eur.:

| Time [min] | pH | Release [%] |
|---|---|---|
| 15 | 1.2 | <1.0 |
| 60 | 1.2 | <1.0 |
| 120 | 1.2 | 1.3 |
| 180 | 6.8 | 99.7 |

Example 4

Coating on Bisacodyl Pellets

| | |
|---|---|
| Emulsion polymer copolymer B | 65.0 g |
| Glycerol monostearate (GMS) | 1.95 g |
| Polysorbat 80 (33% aqueous solution) | 2.36 g |
| Water, purified | 78.9 g | are used to prepare a spray suspension, by emulsifying GMS and Polysorbat 80 at 65° C. in the water and cooling the emulsion to room temperature with stirring. The emulsion polymer is incorporated into this emulsion with stirring.

In a fluidized-bed apparatus (type: Mini Glatt, from GLATT) 150 g of bisacodyl pellets are coated by means of bottom spraying, under the following conditions:

| | |
|---|---|
| Nozzle diameter | 0.5 mm |
| Feed air temperature | 35° C. |
| Product temperature | 31-32.5° C. |
| Spraying pressure | 0.5 bar |
| Spraying rate | 1.6-1.8 g/min |
| Afterdrying | 2 h, at 40° C. on racks |

The polymer add-on was 13%.

The coated bisacodyl pellets gave the following results in the dissolution test according to Pharm. Eur.:

| Time [min] | pH | Release [%] |
|---|---|---|
| 15 | 1.2 | <1.0 |
| 60 | 1.2 | <1.0 |
| 120 | 1.2 | <1.0 |
| 180 | 6.8 | 97.0 |

Example 5

Coating on Caffein Pellets

| | |
|---|---:|
| Emulsion polymer copolymer B | 266.7 g |
| Glycerol monostearate (GMS) | 8.0 g |
| Triethyl citrate | 8.0 g |
| Polysorbat 80 (33% aqueous solution) | 9.7 g |
| Water, purified | 203.6 g | are used to prepare a spray suspension, by emulsifying GMS, triethyl citrate and Polysorbat 80 at 65° C. in the water and cooling the emulsion to room temperature with stirring. The emulsion polymer is incorporated into this emulsion with stirring.

In a fluidized-bed apparatus (type: GPCG 1, from GLATT) 800 g of bisacodyl pellets are coated by means of top spraying, under the following conditions:

| | |
|---|---|
| Nozzle diameter | 1.2 mm |
| Feed air temperature | 39° C. |
| Product temperature | 30° C. |
| Spraying pressure | 1.8 bar |
| Spraying rate | 12.5 g/min |
| Afterdrying | 2 h, at 40° C. on racks |

The polymer add-on was 10%.

The coated caffein pellets gave the following results in the dissolution test according to Pharm. Eur.:

| Time [min] | pH | Release [%] |
|---:|---:|---:|
| 15 | 1.2 | <1.0 |
| 60 | 1.2 | 1.7 |
| 90 | 1.2 | 2.3 |
| 120 | 1.2 | 3.9 |
| 150 | 6.8 | 87.6 |
| 180 | 6.8 | 99.5 |

The invention claimed is:

1. A process for producing a coated drug form or a drug form in the form of an active ingredient matrix, by processing a copolymer, an active pharmaceutical ingredient, a core if present and/or pharmaceutically customary excipients in a conventional manner by melting, injection molding, extrusion, wet granulation, casting, dipping, spreading, spraying or compression to form a coated drug form and/or to form an active ingredient matrix, wherein said copolymer comprises
20 to 33% by weight of methacrylic acid and/or acrylic acid,
5 to 30% by weight of methyl acrylate and
20 to 40% by weight of ethyl acrylate and
more than 10 to 30% by weight of butyl methacrylate and,
0 to 10% by weight of vinylically copolymerizable monomers,
the proportions of the monomers adding up to 100% by weight,
and the glass transition temperature of the copolymer is 55 to 70° C.

2. The process as claimed in claim 1, wherein 5 to 25% by weight of a plasticizer are added to the coating agent and binder.

3. The process as claimed in claim 1, wherein the copolymer is in the form of a dispersion for producing the drug form.

4. The process as claimed in claim 3, wherein the dispersion is obtained by redispersing a freeze-dried or spray-dried copolymer powder.

5. The process as claimed in claim 3, wherein from 2 to 10% by weight of the copolymer is in partly neutralized form.

6. The process as claimed in claim 5, wherein said copolymer is partly neutralized by by adding NaOH.

7. The process as claimed in claim 3, wherein an anionic emulsifier is present in an amount of from 0.1 to 2% by weight.

8. The process as claimed in claim 7, wherein said emulsifier comprises sodium lauryl sulfate.

9. The process as claimed in claim 1, wherein the copolymer, and optionally pharmaceutically customary additives, is processed to form shaped bodies and an active pharmaceutical ingredient is enclosed therein.

10. The process as claimed in claim 9, wherein the shaped body is a capsule, a part of a capsule or a weldable film.

11. A drug form produced by the process as claimed in claim 1.

12. The drug form as claimed in claim 11, wherein the drug form comprises tablets, tablets with delayed or accelerated disintegration, minitablets, pellets, tablets compressed from pellets, pellets as a filling in capsules, granules or minitablets, a transdermal therapy system, capsules, parts of capsules or other drug forms, sachets, dried juices, suppositories, pessaries or implants.

13. The drug form as claimed in claim 11, wherein an active ingredient is present selected from the group consisting of laxatives, analgesics, antibiotics, antirheumatics, antiallergics, antiarrhythmics, antibiotics, antiepileptics, beta-receptor blockers, calcium channel blockers, chemotherapeutics, enzymes, extracts, inhibitors of the rennin-angiotensin system, broncholytics/antasthmatics cholinergics, diuretics, circulation promoters, gout agents influenza agents, coronary agents, osteoporosis agents (biphosphonates), lipid reducers, gastrointestinal agents, peptides, proteins, proton pump blockers, psychopharmaceuticals, platelet aggregation inhibitors urological agents venous therapeutic agents, vitamins and minerals.

14. The drug form as claimed in claim 13, wherein the active ingredient is selected from the group consisting of paroxetine, reboxetine morphine, derivatives of reboxetine morphine, tramadol, bisacodyl, sodium fluoride acamprosate Ca, digitoxin, dimethicone, *coli* bacteria, lipoic acid, methenamine, budenoside, acetylsalicylic acid, diclofenac, flurbiprophen, indometacin, lonazolac, hydrocortisone, ibuprofen, ketoprofen, prednisolone, propyphenazone, naproxen, paracetamol, flurbiprofen, dimetindene, quinidine, metoprolol, propranolol, oxprenolol, pindolol, atenolol, metoprolol, disopyramide, verapamil, diltiazem, gallopamil, nifedipine, nicardipine, nisoldipine, nimodipine, amlodipine, theophylline, salbutamol, terbutaline, ambroxol, aminophylline, carbamazepine, alendronate, etidronate, clodronate, pamidronate, ibandronate, choline theophyllinate, pyridostigmine, piretanide, furosemide, pentoxifylline, naftidrofuryl, buflomedil, xantinol nicotinate, bencyclane, allopurinol, norephedrine, clorphenamine isosorbide mononitrate, isosorbide dinitrate, glycerol trinitrate, molsidomine, bezafibrate, fenofibrate, gemfibrozil, cerivastatin, pravastatin, fluvastatin, lovastatin, atorvastatin, simvastatin, 5-aminosalicylic acid, sulfasalazine, budenoside, natamycin, preglumetacin sulfasalacine, nitrofurantion xantinol, metoclopramid, amitriptyline, dibenzepine, venlafaxin, thioridazine, oxazepam, omeprazole, lanzoprazole, pantoprazole, rabeprazole, perprazole, esomprazole, nitrofurantoin, rutoside, garlic, aescin, bromelaine, pancreatin or trypsin, an insulin, a human growth hormone (hGH), corbaplatin, intron A, calcitonin, cromalyn, an interferon, a calcitonin, granulocyte colony stimulating factor (G-CSF), an interleukin, a kinine, parathyroid hormones, glucagon, pindolol, prosomatostatin, a somatostatin, detirelix, cetrorelix, vasopressin, 1-deaminocysteine-8-D-arginine vasopressin, leuprolide acetate, an antigen obtained from grasses or other plants, IgG, specific vaccines or monoclonal antibodies, dry plant extract, ascorbic acid, aspartamic acid, vaiproic acid zinc, and potassium, sodium, lithium and pharmaceutically acceptable salts thereof.

15. A copolymer capable of producing a drug form as claimed in claim 11.

16. The copolymer as claimed in claim 15, wherein the copolymer is in the form of a partly neutralized powder.

17. The copolymer as claimed in claim 15, wherein the copolymer is in powder form in a mixture with customary pharmaceutical excipients in a redispersible form.

18. A cosmetic or a nutritional supplement comprising the copolymer as claimed in claim 15.

* * * * *